United States Patent [19]

Sherman

[11] Patent Number: 4,626,292

[45] Date of Patent: * Dec. 2, 1986

[54] SOFT CONTACT LENS WETTING AND PRESERVATION METHOD

[75] Inventor: Guy J. Sherman, Mandeville, La.

[73] Assignee: Sherman Laboratories, Inc., Abita Springs, La.

[*] Notice: The portion of the term of this patent subsequent to Jan. 4, 2000 has been disclaimed.

[21] Appl. No.: 667,120

[22] Filed: Nov. 1, 1984

Related U.S. Application Data

[60] Division of Ser. No. 537,245, Sep. 28, 1983, Pat. No. 4,528,535, which is a continuation-in-part of Ser. No. 384,110, Jun. 1, 1982, abandoned, which is a continuation-in-part of Ser. No. 53,758, Jul. 2, 1979, abandoned.

[51] Int. Cl.$^4$ .......................... C11D 3/48; C11D 1/72
[52] U.S. Cl. ........................................ 134/26; 134/3; 134/28; 252/106; 252/153; 252/173; 252/174.21; 252/174.22; 252/542; 252/545; 252/546; 252/DIG. 14; 422/28; 422/40
[58] Field of Search ............................ 134/2, 3, 26, 28; 252/106, 153, 542, 545, 546, 173, 174.21, 174.22, DIG. 14; 422/28, 40

[56] References Cited

U.S. PATENT DOCUMENTS

| | | | |
|---|---|---|---|
| 3,882,036 | 5/1975 | Krezanoski et al. | 252/106 |
| 4,013,576 | 3/1977 | Loshaek | 252/106 |
| 4,127,423 | 11/1978 | Rankin | 252/106 X |
| 4,367,157 | 1/1983 | Sherman | 252/106 |
| 4,510,065 | 4/1985 | Sherman | 252/106 |
| 4,529,535 | 7/1985 | Sherman | 252/106 |
| 4,551,461 | 11/1985 | Sherman | 422/28 X |
| 4,560,491 | 12/1985 | Sherman | 422/28 X |

*Primary Examiner*—Barry S. Richman
*Assistant Examiner*—B. P. Heaney
*Attorney, Agent, or Firm*—Jenner & Block

[57] ABSTRACT

Preservative systems which may be incorporated into aqueous compositions for the wetting and re-wetting of contact lenses and especially silicone copolymer (gas-permeable) and soft contact lenses are provided. The preservative system includes trimethoprim, a salt of EDTA and sorbic acid or ascorbic acid as adjuvant bactericides. The use of preservatives which are known to cause eye irritation, such as thimerosal, benzalkonium chloride and chlorhexidine is eliminated. Wetting and re-wetting compositions which incorporate the preservative system and include thickening and wetting agents are also provided. The wetting and re-wetting solutions can be instilled directly into the eye during contact lens wearing periods and are especially useful for wetting silicone copolymer contact lenses. A method of wetting silicone copolymer lenses is also provided.

1 Claim, No Drawings

SOFT CONTACT LENS WETTING AND PRESERVATION METHOD

RELATED APPLICATION

This is a division of application Ser. No. 537,245, filed Sept. 28, 1983, now U.S. Pat. No. 4,529,535, which is a continuation-in-part application of U.S. patent application Ser. No. 384,110, filed June 1, 1982, now abandoned, which is a continuation-in-part application of U.S. patent application Ser. No. 53,758, filed July 2, 1979, now abandoned.

BACKGROUND OF THE INVENTION

Just as there are marked differences in the structure and composition of hard contact lenses, cellulose acetate butyrate (CAB) and silicone copolymer gas-permeable contact lenses and soft contact lenses, there are also marked differences in the maintenance, care and treatment of the various types of hard, CAB, silicone and soft lenses. While patient care and treatment of hard contact or conventional contact lenses is relatively simple and uncomplicated, the proper care and treatment of CAB and silicone copolymer lenses (gas-permeable) and the newer soft and hydrophilic lenses has proved to be more complex, time consuming and costly to the patient.

The primary difference between the conventional hard contact lens and the silicone copolymer lenses and the more complex soft lenses is the hydrophobic nature of the silicone copolymer lenses and the marked increase in the polar or water attracting centers of the hydrophilic gel material from which the soft contact lenses are made. It is this property of the hydrophilic gel lens that gives the soft lens its own unique physical properties and clinical behavior. This polar or water attracting center of the gel material is represented in the hydroxyethyl methacrylate bond as a hydroxyl group (—OH) which attracts and holds large amounts of water. It is this high water content held in the expanded matrix of the hydrophilic gel lens which leads to the special difficulties in cleaning and disinfecting or asepticising the soft hydrophilic lens. The hydrophilic nature of soft contact lenses makes the lenses vulnerable to bacterial contamination. While studies have demonstrated that bacteria cannot penetrate the actual intromolecular pores of the hydrophilic lens, except in defective lenses, the bacteria have an affinity for protein and tear deposits on the surfaces of the lens matrix. In particular, the tears and fluids absorbed by the soft lenses serve as excellent bacterial culture media. If defects or nicks occur in the lenses either during manufacture or subsequent patient wear, bacteria may find a haven to grow and be sheltered from superficial lens cleaning and disinfection.

Potentially harmful fungi are also a possible danger to the soft contact lens. Fungi, like bacteria, can thrive in tear secretions, other fluids or deposits and penetrate the lens material directly if enzymatic degradation of the lens material has taken place.

Similarly, any substantial residual proteinaceous or tear secretion deposits or lipid deposits remaining in or on the lens may readily overwhelm and inactivate the most effective germicidal components of a disinfecting system, and may thus serve to act as a growth media for a variety of potentially harmful microorganisms and fungi. Therefore, it is important that prior to storing the soft contact lenses in a disinfecting solution, protein and lipid deposits be removed from the lens surfaces so that the disinfectant properties of the sterilizing solution or method will not be overwhelmed by gross organic or inorganic deposits and pollutants. Therefore, an effective cleaning step or steps is an essential and mandatory part of any effective soft lens treatment and maintenance regimen.

Wetting solutions are used to prepare the contact lenses prior to insertion into the eye and are known in the prior art. Prior art contact lens wetting solutions have primarily involved the use of polyvinyl alcohol as a wetting agent and methyl cellulose or hydroxyethyl cellulose as viscosity building agent. These prior art solutions have also contained sufficient amounts of water-soluble salts, generally sodium chloride, to make them isotonic or hypertonic with human serum and tear fluid. For example, hypertonic wetting solutions are disclosed in U.S. Pat. No. 3,549,747.

Re-wetting solutions are instilled directly into the eyes when contact lenses are being worn. Such solutions can also be used before or after wearing periods. The purpose of re-wetting solutions include providing comfort and relubrication for the eye.

Because of the potential for bacterial contamination, wetting and re-wetting solutions generally include a preservative system to prevent or inhibit microbial growth, especially where multi-dose containers of the solution are prepared. Generally, where no preservative is employed, single dose containers are utilized, which result in greater expense.

Preservative systems known in the prior art for wetting solutions are disclosed in U.S. Pat. No. 3,549,747. Known preservatives include benzalkonium chloride, thimerosal and chlorhexidine. However, these compounds have drawbacks in that they can be concentrated in the lens matrix and cause irritation, excessive burning and red eye, which can prevent the patient from wearing the lenses or can otherwise be hypersensitive to the eye.

With the advent of extended wear contact lenses, it becomes even more important to avoid such problems, since those lenses can remain in the eye for several weeks. Thus, a need has arisen for an effective preservative system which avoids the use of preservatives known to cause eye irritation and which is suitable for soft contact lenses in a wetting and re-wetting solution. A need also exists for a soft contact lens wetting and re-wetting solution which incorporates such a preservative system. Finally, a need exists for an "in-eye" re-wetting solution that can be instilled directly into the eyes to provide re-lubrication and comfort for the eyes having such a preservative system.

SUMMARY OF THE INVENTION

This invention relates to novel and effective silicone copolymer (gas-permeable) contact lens and soft contact lens preservative systems and wetting and re-wetting solutions. More particularly, this invention relates to highly effective silicone copolymer and soft contact lens wetting and re-wetting solutions that can be applied directly into the eye that include a preservative system which avoids hypersensitivity problems associated with preservative systems containing thimerosal or chlorhexidine, for example. The invention is especially suitable for use with CAB, silicone copolymer and soft lenses (such as HEMA contact lenses, for example) including extended wear contact lenses, and reference to soft lenses includes CAB, silicone copolymer and extended wear lenses. The invention is also suitable for use in connection with hard contact lenses. In fact, the wetting and re-wetting solution can be used directly in the eye by persons who do not wear contact lenses, such as for relief of dry eye syndromes, idiopathic ocular discomfort and other conditions. As used hereinafter and in the claims, the term "wetting solution" or "wetting composition" includes re-wetting solutions or compositions that are suitable for application directly into the eye.

In another aspect, this invention relates to a contact lens wetting and re-wetting composition that effectively wets the surface of contact lenses, especially silicone copolymer and soft and extended wear contact lenses. The solution is also useful as an in-eye comfort solution during and after contact lens wearing periods. The solution can also be used as an in-eye comfort solution whether or not contact lenses are worn.

In accordance with the invention, a preservative system is provided that is incorporated in a contact lens wetting and/or re-wetting solution. The preservative system is effective for maintaining the solution sterile, preventing bacteria and other organisms from contaminating the solution after its container has been opened and an initial use has been made of a portion of the solution, for example. While intended primarily for use in connection with soft contact lenses, including extended wear lenses, the preservative system may also be used with hard contact lenses.

The preservative system of the invention is safe and effective, is not deleterious to the human eye or ocular tissue, and when present in a wetting solution, can be instilled directly into the eye. Further, the preservative system does not discolor soft contact lenses and is not otherwise deleterious to soft lenses. Accordingly, the shortcomings of preservative systems containing compounds such as thimerosal or chlorhexidine, for example, are avoided.

The preservative system of the invention for maintaining sterility in a contact lens wetting composition which can be instilled into the eye includes trimethoprim and adjuvant bactericides which include ethylenediaminetetraacetic acid (EDTA) or a water soluble salt thereof and sorbic acid. The components are present together in effective amounts for maintaining the sterility of the composition. Usually, an effective amount of trimethoprim is from about 0.05% to about 2.0% by weight of the total wetting composition. Generally, an effective amount of EDTA is from about 0.025% to about 0.5% and an effective amount of sorbic acid is generally from about 0.001% to about 0.20%, all by weight of the total composition. A lower useful range of sorbic acid is from about 0.001% to about 0.10% by weight. Ascorbic acid, or a salt thereof, may be utilized in place of or in addition to sorbic acid. The ascorbic acid or salt thereof may be present in an effective amount, usually of from about 0.1% to about 10% calculated as ascorbic acid. Suitable salts of ascorbic acid include the sodium and calcium salts thereof. While greater amounts than specified could be used, cost or eye comfort could be a limiting factor.

In accordance with another aspect of the present invention, a method is provided for maintaining the sterility of contact lens wetting compositions which method includes providing in the compositions a preservative system in accordance with the invention. The sterility of the composition is preserved while avoiding the use of bactericides which are absorbed by soft lenses and which are incompatible with ocular tissue or otherwise cause eye irritation and/or lens discoloration.

In accordance with the preferred aspects of the present invention, a composition suitable for wetting and re-wetting contact lenses is provided.

The wetting composition includes a preservative system and a wetting system. Preferably, the aqueous wetting composition according to the invention that includes a wetting system and a preservative system has a tonicity of from about 1.0 to about 2.0 and a pH of from about 6.0 to about 7.0.

In accordance with one embodiment of the invention, an aqueous wetting composition is provided that is especially suitable for wetting soft contact lenses. The wetting composition contains a preservative system of the above description and a wetting component or components. Any suitable wetting component may be utilized that is suitable for wetting contact lenses. If the wetting composition is intended for wetting soft contact lenses, then the wetting component should be suitable for use with soft contact lenses.

Generally, the wetting system should be completely miscible with water at the utilized concentrations and generally should also provide a clear solution. In addition, the wetting system must not act adversely with the type of contact lens with which use is intended, nor with other materials present in the solution and, finally, must not irritate the eye.

The wetting system includes at least one component suitable for wetting contact lenses. Usually, the wetting system will include a viscosity-building agent and a wetting agent suitable for soft contact lenses. Suitable viscosity-building agents include water soluble cellulosic polymers, which may be synthetic or natural, for example. Such materials also assist in wetting the lenses. Suitable wetting agents include polyvinyl alcohol and polyvinylpyrrolidone and mixtures thereof, for example. Other suitable viscosity-building agents and wetting agents for contact lens wetting solutions will be known to those skilled in the art.

Suitable cellulosic polymers include hydroxyethylcellulose, methylcellulose, carboxymethylcellulose, natural gums and mixtures thereof. Usually, the amount of cellulosic polymer present in the composition is from about 0.05% to about 0.80% by weight of the total composition.

Usually, the wetting composition will have a viscosity of about 20 to 30 cps at 25° C. Medium grade cellulosic polymers are useful for achieving the desired viscosity.

Preferably, the polyvinyl alcohol utilized is fully hydrolized. Generally, the amount of polyvinyl alcohol present in the composition is from about 0.5% to about 2.5% by weight of the total composition.

Preferably, an additional wetting compound, a polyvinylpyrrolidone polymer, will be utilized, usually in an amount of from about 0.5% to about 2.0% by weight of the total composition.

It is to be understood that the invention is not limited to the foregoing types of wetting agents and viscosity building agents. Any type of material which can be used to provide the desired wetting action and which is compatible with the preservative system of the present invention and is otherwise suitable for use in a wetting solution or a contact lens wetting solution can be utilized.

Compositions in accordance with the invention have a pH of preferably from about 6.0 to about 7.0. This slightly acidic or neutral pH helps to prevent irritation upon instillation into the eyes. Sodium bicarbonate may be present in the composition, generally from about 0.01% to about 3.0% by weight of the total composition for adjustment of pH.

The soft contact lens wetting or in-eye comfort drop composition according to the invention preferably will have a tonicity of from about 1.0 to about 2.0. Thus, the compositions of the invention are mildly hypertonic to help prevent possible absorption into the lens matrix of foreign matter, bacteria or other residue which could build up and cause contamination problems and deterioration and discoloration of the lens itself. The remainder of the composition is purified water U.S.P.

The wetting compositions of the invention containing polyvinyl alcohol, polyvinylpyrrolidone and/or a cellulosic polymer of the type described are especially useful for wetting silicone copolymer contact lenses after the lenses have been cleaned with a nonionic detergent cleaner suitable for cleaning the lenses such as a cleaner of the type disclosed in U.S. patent application Ser. No. 384,110, filed June 1, 1982, now abandoned, and Applicants U.S. patent application Ser. No. 537,257, filed Sept. 28, 1983, now U.S. Pat. No. 4,510,065, the disclosures of which are hereby incorporated by reference.

Particularly where silicone co-polymer lenses are concerned, it must be pointed out that polyvinyl alcohol and polyvinylpyrrolidone, or other typical synthetic wetting agents and/or even the natural tear itself will not adequately wet this type of contact lens when a surface charge or static electricity charge is present on the lens. A lens that is not adequately wetted cannot be worn comfortably or provide clear vision. This wetting rejection phenomenon is not related to the lens being incompatible with the tear or heretofore proven wetting agents, such as polyvinyl alcohol or polyvinylpyrrolidone. The surface charge or static electricity charge on the lens prevents adequate wetting by an artificial wetting agent or the natural tear.

It has been discovered that the surface charge or static electricity charge which may be present on silicone copolymer lenses is eliminated or neutralized by suitable nonionic detergents and makes the lenses wettable by the aforesaid wetting compositions of the present invention. Failure to eliminate or neutralize such charges can prevent such lenses from being adequately wetted.

Thus, in accordance with another aspect of the present invention, a method of wetting a silicone copolymer contact lens having a surface charge is provided that comprises neutralizing or eliminating the surface charge and contacting the lens with a wetting composition containing at least one wetting component selected from polyvinyl alcohol, polyvinylpyrrolidone and a cellulosic polymer. Suitable wetting components are as previously described herein. One procedure by which the surface charge can be neutralized or eliminated is by contact with nonionic detergent material as aforesaid. The nonionic detergent material is then rinsed from the lens prior to wetting. Suitable nonionic detergents include the hydroxyalkylated and polyoxyalkylated surfactants as described in U.S. patent application Ser. No. 384,110, now abandoned, and in U.S. patent application Ser. No. 537,257, now Pat. No. 4,510,065. The preferred non-ionic detergents are a combination of a polyoxypropylene-polyoxyethylene block copolymer, an amphoteric surface active agent and an alkylaryl polyether alcohol as described in U.S. Ser. No. 384,110, now abandoned, and in U.S. patent application Ser. No. 537,257, now Pat. No. 4,510,065. Reference is also made thereto for the concentrations of the surfactants and other components which may be present in the cleaner composition.

DETAILED DESCRIPTION OF THE INVENTION

According to the invention, the preservative system, which provides antibacterial and antifungal activity, includes from about 0.05% to about 2.0% trimethoprim, preferably from about 0.075% to about 0.3% and most preferably about 0.1% by weight of the total composition. Trimethoprim is also known as 2,4-Diamino-5-(3,4,5-trimethoxybenzyl)pyrimidine and as syraprim. See, for example, *The Merck Index*, eighth edition, pg 1,077.

Adjuvant bactericides are also present in the preservative system, which usually includes from about 0.025% to about 0.5%, preferably 0.1%, by weight of the total composition of ethylenediaminetetraacetic acid or a water soluble salt thereof which has bactericidal properties. The other adjuvant bactericide present is sorbic acid, generally present in an amount of from about 0.001% to about 0.20% and preferably about 0.125% by weight of the total composition. Sorbic acid is believed necessary to kill *Pseudomonas aeruginosa* bacteria, to which contact lenses and cleaning solutions are susceptible to exposure. Other types of bacteria and other organisms to which the solutions are susceptible to exposure and which are necessary to protect against are adequately rendered inactive or killed by the trimethoprim, the effectiveness of which is enhanced by the presence of EDTA and sorbic acid. While sorbic acid has antibacterial and antifungal properties, being active against molds and yeasts and to a lesser degree against bacteria, its maximum effectiveness is usually achieved at a pH of about 4.5. As the pH increases, the effectiveness of sorbic acid decreases, and at a pH of about 6.5 or more, it is not particularly effective and is not suitable as a primary antibacterial agent for solutions of the invention. However, sorbic acid has been found to act as an adjuvant bactericide for trimethoprim.

The inclusion of ethylenediaminetetraacetic acid or a water soluble salt of ethylenediaminetetraacetic acid serves as a buffering and preservative component of the composition according to the invention, and has also been demonstrated to have antibacterial and antifungal properties. The preferred salt of ethylenediaminetetraacetic acid is disodium ethylenediaminetetraacetate (disodium EDTA or disodium edetate). Other salts of EDTA which may be utilized include, for example, mono-, di-, tri- and tetra-alkali metal salts.

The ascorbic acid compound which may be present in the preservative system in place of or in addition to sorbic acid is present in a concentration sufficient to preserve the sterility of solutions for contact lenses when combined with the other components of the preservative system. Generally, an amount of between about 0.1% and 10% by weight of the total composition calculated as ascorbic acid is a sufficient concentration to preserve sterility. Usually, the amount of ascorbic acid will be less than about 5% by weight of the total solution composition. The actual weight percent of the ascorbic acid salt will be that weight percent of salt required to achieve a molar concentration of the ascorbic acid ion that is equal to the molar concentration of ascorbic acid at a given weight percent. For example, if it is desired to produce a solution of an ascorbic acid salt equivalent to 10% by weight ascorbic acid, the molar concentration "x", of a 10% by weight solution of ascorbic acid is computed. The weight percent of the ascorbic acid salt required to provide an ascorbic acid ion molar concentration of that amount, "x", is the actual weight percent of the ascorbic acid salt that is utilized. It is known that ascorbic acid is readily oxidized. Therefore, the sodium salt of ascorbic acid is preferably utilized, sodium ascorbate.

In D value studies to demonstrate the log kill of microorganisms ascorbic acid at concentrations of 1.0% to 5.0% was shown to produce a significant log kill of 5 selected microorganisms, including *Psuedomonas aeruginosa* and *Stephylococcus aureus* within a six hour time period. Since ascorbic acid is naturally present in the human body and is nontoxic to ocular tissue in relatively large amounts, it is believed to be safe and efficacious ingredient.

When ascorbic acid is utilized, preferably monothioglycerol is included in an amount effective to stabilize the ascorbic acid compound. Most preferably, in this embodiment monothioglycerol is present in a weight ratio of monothioglycerol to the ascorbic acid compound, calculated on the basis of ascorbic acid, of 1:50. Thus, for example, if the concentration of the ascorbic acid compound is 10%, calculated on the basis of ascorbic acid, the concentration of monothioglycerol is 0.2% by weight.

When ascorbic acid is utilized in the preservative system, in order to increase the shelf life, the compositions are formulated and packaged in an atmosphere that is substantially devoid of free oxygen. For example, the compositions can be formulated and sealed in sterile containers, in the presence of a nitrogen or carbon dioxide atmosphere. Further, it is advantageous for the ascorbic acid compound to be packaged in a non-transparent container to reduce degradation that can be caused by ultraviolet radiation. The ascorbic acid could also be packaged separately, until the time of use, for example.

Any suitable wetting system can be used in accordance with the invention. The preferred wetting system contains a wetting agent and a viscosity building agent. An especially preferred wetting system contains hydroxyethylcellulose, polyvinylpyrrolidone and polyvinyl alcohol. A preferred hydroxyethylcellulose is available from Hercules, Inc. of Wilmington, Del. under the trade designation "250 H." A preferred polyvinylpyrrolidone is available from GAF Corporation of New York, N.Y. under the name Plasdone ® C. A preferred polyvinyl alcohol is available from the Monsanto Company of St. Louis, Mo. under the name of "Galvatol" which is partially hydrolized.

The wetting compositions of the present invention are preferably buffered and slightly acid or neutral. The preferred pH range is from about 6.0 to about 7.0. Suitable buffers are known in the art. Especially suitable buffers include sodium bicarbonate and tribasic sodium phosphate ($Na_3PO_4 \cdot 12H_2O$). The preferred combination of buffers is sodium bicarbonate, tribasic sodium phosphate and sodium biphosphate ($NaH_2PO_4$)$\cdot H_2O$, in amounts to provide and maintain the desired pH.

The remainder of the wetting composition is purified water U.S.P. and preferably includes combinations of essentially netural and alkaline salts compatible with ocular tissue and soft contact lens material which are water soluble, generally present in a concentration to provide an aqueous composition salt content equivalent to from about 1.0 to about 2.0 tonicity. Thus, the soft contact lens solutions of the present invention can be mildly hypertonic which helps in the prevention of possible absorption into the lens matrix of foreign matter, protein, lipids and bacteria which could build up and cause contamination problems and deterioration and discoloration of the lens itself. Sodium chloride can be present in the soft contact lens composition in an amount from about 0.05% to about 2.0% by weight of the total aqueous composition, for example, and preferably in an amount of about 0.75% by weight of the total aqueous composition. Potassium chloride is another salt which is preferably used in conjunction with sodium chloride and should generally be present in an amount of from about 0.05% to about 2.0% by weight of the total aqueous composition and preferably in an amount of about 0.28% by weight of the total aqueous composition.

An especially preferred wetting composition is:

| Component | Amount (% by weight) |
|---|---|
| Sodium bicarbonate | 0.050 |
| Sodium phosphate (tribasic) | 0.028 |
| Sodium biphosphate | 0.028 |
| Sodium chloride | 0.748 |
| Potassium chloride | 0.280 |
| Disodium EDTA | 0.100 |
| Hydroxyethylcellulose 250H | 0.450 |
| Polyvinyl alcohol | 1.000 |
| Polyvinylpyrrolidone (Plasdone ® C) | 0.500 |
| Trimethoprim | 0.100 |
| Sorbic acid | 0.125 |
| Purified water | Balance to 100 |

While the present invention has been described primarily with respect to wetting solutions, the wetting compositions of the invention containing a water soluble cellulosic polymer, polyvinyl alcohol and polyvinylpyrrolidone and preservative system are especially useful for application directly into the eyes while contact lenses are being worn for effective relubrication and immediate restoration of comfort when applied to eyes which are dry, tight and/or uncomfortable. Such compositions further reduce the tendency of oil and mucous deposits to accumulate on contact lenses. These compositions are especially suitable for use with silicone copolymer contact lenses and soft contact lenses.

Suitable nonionic detergents and compositions for neutralizing the surface charge on silicone copolymer lenses are hereinafter described. A preservative system and salts similar to those described herein may also be incorporated into the compositions.

One non-ionic detergent system which may be used to neutralize surface charges contains three different types of non-ionic surface acting agents or detergents, each of which should be compatible with the contact lens material. The synergistic effect of the combined detergents also causes both proteins and lipids to be removed from the lens surfaces when the cleaning composition according to the invention is used. The three types of non-ionic detergents preferably utilized are: (1) a polyoxypropylene-polyoxyethlene block copolymer; (2) an amphoteric surface active agent; and (3) an alkylaryl polyether alcohol. Satisfactory results can also be obtained with the following two types of non-ionic detergents: (1) an amphoteric surface active agent; and (2) an alkylaryl polyether alcohol.

The block copolymer is a polyoxypropylene-polyoxyethylene block copolymer which is compatible with soft contact lenses. Suitable block copolymers have a molecular weight of about 1,100 to about 14,000 and a water solubility in excess of 10 grams per 100 milliliters. Preferably, about 70% to about 85% of the total molecular weight of the block copolymer consists of the hydrophilic polyoxyethylene group with the remaining weight of the molecule representing the hydrophobic polyoxypropylene base and posseses relatively low foaming characteristics.

One group of block copolymers suitable for use are those sold by BASF Wyandott Corporation of Wyandott, Mich., under the trademark "Pluronic." The following Pluronic block copolymers are suitable for use and are set forth for example and not limitation: Pluronic F-68, Pluronic F-77, Pluronic P-75, Pluronic P-65, Pluronic L-64, Pluronic F-87, Pluronic F-88, Pluronic F-98, Pluronic F-108 and Pluronic F-127. The block copolymer is generally present in an amount of from about 1.0 to about 15.0% by weight of the total aqueous composition, and preferably comprises about 6.0% by weight of the total aqueous composition. Preferably, the block copolymer has relatively low foaming characteristics.

The preferred type of amphoteric surface active agent is 2-Cocoyl-2-imidazolinium lauryl sulfate-1-carboxymethyloxyethyl-1-carboxymethyl disodium which is also sold under the trade name "Miranol 2 MCA Modified" by the Miranol Chemical Company, Inc. of Irvington, N.J. The amphoteric surface active agent is preferably used in an amount of from about 0.5% to about 8.0% of the total weight of the cleaner composition and preferably comprises about 3.0% of the total aqueous composition. One substitute for "Miranol 2 MCA Modified" is "Miranol MHT" which is also sold by the Miranol Chemical Company, Inc.

The third type of non-ionic detergent which may be present in the detergent system is an alkylaryl polyether alcohol. The preferred type of alkylaryl polyether alcohol is isooctylphenoxypolyethoxyethanol. The most preferred type of isooctylphenoxypolyethoxyethanol contains about 9 units of ethoxyethanol per unit of isooctylphenol and has a molecular weight of about 630. The most preferred alkylaryl polyether alcohol is sold under the trade name "Triton X-100" by the Rohm & Hass Company of Philadelphia, Pa. The alkylaryl polyether alcohol is generally present in a concentration of from about 0.005% to about 5.0%, and preferably about 1.0%, by weight of the total cleaner composition. The alkylaryl polyether alcohols are also known as octylphenolethyleneoxide. The alkylaryl polyether alcohol complements the cleansing characteristics of the block copolymers and helps to remove ocular secretions, proteinaceous deposits and other materials which may be deposited upon the surfaces of the lens.

The remainder of the cleaner composition is purified water U.S.P. and can include combinations of essentially neutral and alkaline salts compatible with ocular tissue and soft contact lens material.

Whereas the present invention has been described with respect to specific embodiments thereof, it will be understood that various changes and modifications will be suggested to one skilled in the art and it is intended that the invention encompass such changes and modifications as fall within the scope of the appended claims.

I claim:

1. A method of wetting a silicone copolymer contact lens having a surface charge, said method comprising:
neutralizing said surface charge and contacting the lens with a wetting composition, said wetting composition includes a wetting system and a preservative system, said wetting system comprising a wetting agent selected from the group consisting of polyvinyl alcohol, polyvinylpyrrolidone, and mixtures thereof, and said preservative system comprising from about 0.05% to about 2.0% trimethoprim by weight of the total composition, a first adjuvant bactericide comprising from about 0.025% to about 0.5% ethylenediaminetetraacetic acid or a water soluble salt thereof by weight of the total composition and a second adjuvant bactericide comprising from about 0.001% to about 0.20% sorbic acid by weight of the total composition.

* * * * *